United States Patent
Tabuse et al.

(10) Patent No.: US 10,160,153 B2
(45) Date of Patent: Dec. 25, 2018

(54) RESIN PELLETIZER DEVICE AND CAVITATION MONITORING METHOD

(71) Applicant: Kabushiki Kaisha Kobe Seiko Sho (Kobe Steel, Ltd.), Kobe-shi (JP)

(72) Inventors: Ryo Tabuse, Kobe (JP); Eiji Takahashi, Kobe (JP); Chitaka Manabe, Kobe (JP); Kaname Araki, Kobe (JP); Shin Iwasaki, Takasago (JP); Tatsuru Miyamoto, Takasago (JP)

(73) Assignee: Kobe Steel, Ltd., Kobe-shi (JP)

( * ) Notice: Subject to any disclaimer, the term of this patent is extended or adjusted under 35 U.S.C. 154(b) by 121 days.

(21) Appl. No.: 15/450,262

(22) Filed: Mar. 6, 2017

(65) Prior Publication Data

US 2017/0259484 A1 Sep. 14, 2017

(30) Foreign Application Priority Data

Mar. 14, 2016 (JP) .................. 2016-049883

(51) Int. Cl.
*B29B 9/06* (2006.01)
*B29C 47/00* (2006.01)
*G01N 29/48* (2006.01)
*G01N 29/04* (2006.01)
*B29C 47/92* (2006.01)
(Continued)

(52) U.S. Cl.
CPC .............. *B29C 47/92* (2013.01); *B29B 9/065* (2013.01); *B29C 47/0066* (2013.01); *G01N 29/04* (2013.01); *G01N 29/48* (2013.01); *B29C 47/0011* (2013.01); *B29C 47/0014* (2013.01); *B29C 47/30* (2013.01); *B29C 2947/92466* (2013.01); *B29L 2031/757* (2013.01)

(58) Field of Classification Search
CPC ................ B29C 47/0066; B29C 47/92; B29C 2947/92466; B29C 47/0011; B29C 47/0014; G01N 29/04; G01N 29/48; B29B 9/065; B29L 2031/757
USPC ......................................................... 73/579
See application file for complete search history.

(56) References Cited

U.S. PATENT DOCUMENTS

| | | | |
|---|---|---|---|
| 3,230,582 A | | 1/1966 | Hoffman et al. |
| 4,221,470 A | * | 9/1980 | Weeks ..................... B01J 3/004 359/894 |

(Continued)

FOREIGN PATENT DOCUMENTS

| | | |
|---|---|---|
| DE | 1454754 | 3/1969 |
| DE | 600 33 413 T2 | 10/2007 |

(Continued)

*Primary Examiner* — J M Saint Surin
(74) *Attorney, Agent, or Firm* — Oblon, McClelland, Maier & Neustadt, L.L.P.

(57) ABSTRACT

Provided is a resin pelletizer device capable of monitoring cavitation. A resin pelletizer device (100) includes a die (6) including a die surface (61) in which die holes (63) are formed, rotary blades (21) that rotate on the die surface (61) in the water, thereby cutting resin extruded from the die holes (63) in the water into a pellet form, a sensor (150) that detects an elastic wave generated during the rotation of the rotary blades (21) on the die surface (61), and a determination unit (121) that monitors an output value of the sensor (150), and determines that cavitation occurs when the output value of the sensor (150) becomes less than a predetermined threshold.

6 Claims, 5 Drawing Sheets

(51) Int. Cl.
*B29L 31/00* (2006.01)
*B29C 47/30* (2006.01)

(56) References Cited

U.S. PATENT DOCUMENTS

| | | | |
|---|---|---|---|
| 4,300,877 A * | 11/1981 | Andersen | B29B 9/065 |
| | | | 264/142 |
| 6,551,087 B1 | 4/2003 | Martin | |
| 7,121,181 B2 * | 10/2006 | Williams | B26D 1/29 |
| | | | 83/663 |
| 2003/0185923 A1 | 10/2003 | Martin | |
| 2006/0167659 A1 * | 7/2006 | Miyasaka | B61F 15/20 |
| | | | 702/185 |
| 2011/0031337 A1 | 2/2011 | Pfeiffer et al. | |
| 2013/0259963 A1 | 10/2013 | Pinchot | |
| 2018/0211851 A1 * | 7/2018 | Kaminaga | H01L 21/67092 |

FOREIGN PATENT DOCUMENTS

| | | |
|---|---|---|
| DE | 10 2008 020 502 A1 | 10/2009 |
| JP | 2001-38676 | 2/2001 |

* cited by examiner

F I G. 1
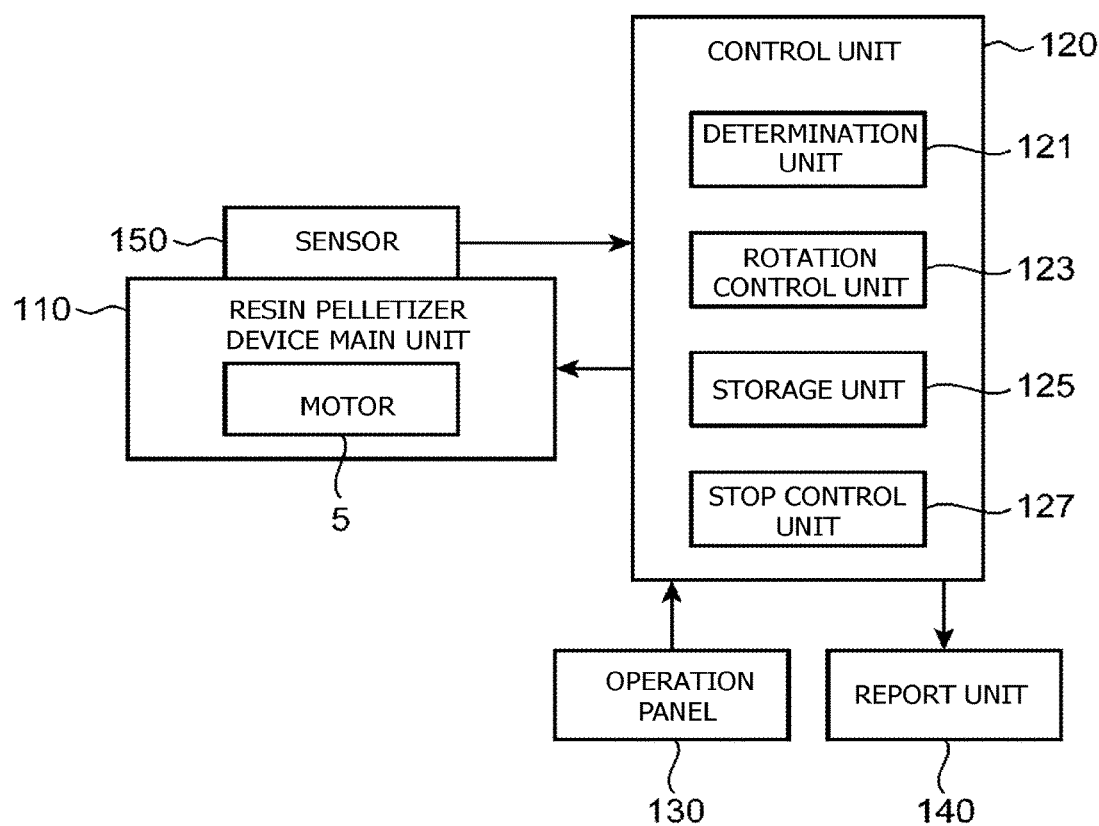

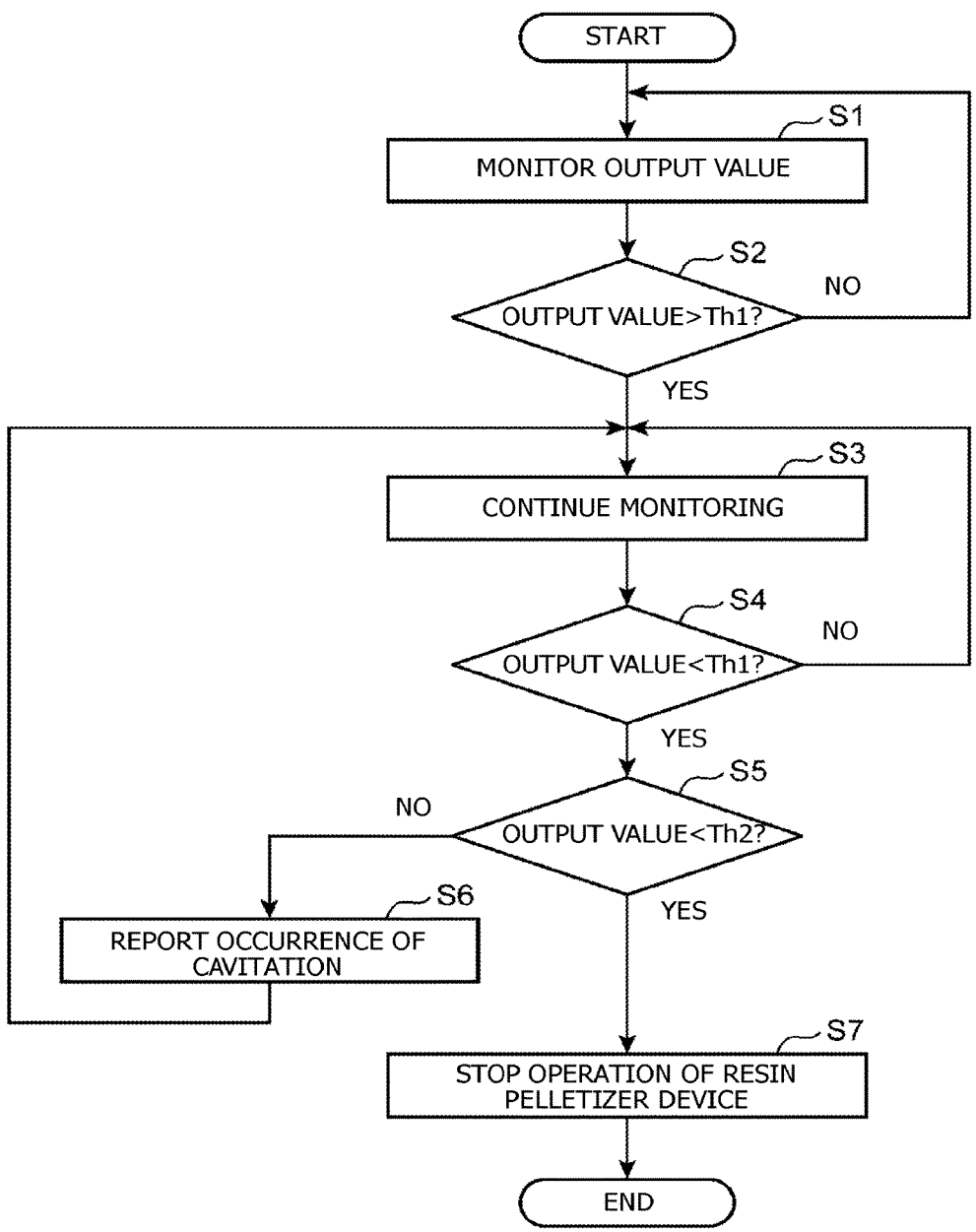

RESIN PELLETIZER DEVICE AND CAVITATION MONITORING METHOD

BACKGROUND OF THE INVENTION

Field of the Invention

The present invention relates to a technology of forming resin into pellets.

Description of the Related Art

A resin pelletizer device is a device that uses rotary blades rotating at a high speed on a die surface through which die holes are formed to cut a molten resin in a strand form (string form) extruded from the die holes into the water, thereby forming the resin into pellets.

A clearance is provided between the die surface and the rotary blades. When the clearance increases, defective cutting of the molten resin occurs. Defective cutting is an occurrence of a pellet having tails or a plurality of pellets connected in a chain form, for example.

As a technology capable of monitoring the clearance, proposed is a defective cutting detection method comprising the following steps: abutting a cutter knife against a die surface, thereby measuring the position of the cutter knife at each reference position setting timing, and setting the measured position as a reference position; measuring the position of the cutter knife while rotating the cutter knife to cut molten resin, and setting the measured position as a present position; and releasing an alarm of defective cutting when a difference between the present position and the reference position becomes more than a predetermined clearance setting value (refer to JP 2001-38676 A, for example).

The resin pelletizer device rotates the rotary blades on the die surface at a high speed in the water, thereby cutting the molten resin, but cavitation may occur on this occasion. The cavitation is such a physical phenomenon that generation and extinction of bubbles occur in a short period due to a pressure difference in a flow of a fluid. The present inventor has found that defective cutting is caused by the cavitation. A technology is desired to permit monitoring the cavitation during the operation of the resin pelletizer device is desired.

SUMMARY OF THE INVENTION

An object of the present invention is to provide a resin pelletizer device capable of monitoring the cavitation and a cavitation monitoring method.

A resin pelletizer device according to a first aspect of the present invention includes a die including a die surface in which a die hole is formed, a rotary blade that rotates on the die surface in the water, thereby cutting resin extruded from the die hole in the water into a pellet form, a sensor that detects an elastic wave generated during the rotation of the rotary blade on the die surface, and a determination unit that monitors an output value of the sensor, and determines cavitation occurs when the output value of the sensor becomes less than a predetermined threshold.

The elastic wave (such as an ultrasonic wave and a vibration) generated while the rotary blade is rotating on the die surface is detected by the sensor. The present inventor has found such a phenomenon that the output value of the sensor increases as the rotation number of the rotary blade increases, but the output value of the sensor decreases as the cavitation occurs. This is caused by fluttering of the rotary blade as a result of the occurrence of the cavitation.

The cavitation causes defective cutting. Thus, the determination unit monitors an output value of the sensor, and determines that the cavitation occurs when the output value of the sensor becomes less than the predetermined threshold. Thus, with the resin pelletizer device according to the first aspect of the present invention, the cavitation can be monitored.

In the above-mentioned configuration, the resin pelletizer device further includes a report unit that reports the occurrence of the cavitation when the determination unit determines that the cavitation occurs.

This configuration reports the occurrence of the cavitation when the cavitation is determined to occur. Thus, an operator of the resin pelletizer device can take a necessary action (such as an action of decreasing the rotation number of the rotary blade and an action of stopping the operation of the resin pelletizer device) for coping with the cavitation occurrence.

In the above-mentioned configuration, the resin pelletizer device further includes a stop control unit that stops the operation of the resin pelletizer device when the determination unit determines that the cavitation occurs.

This configuration automatically stops the operation of the resin pelletizer device when the cavitation is determined to occur.

In the above-mentioned configuration, the determination unit sets a first threshold and a second threshold less than the first threshold as the thresholds, and compares the thresholds with the output value of the sensor, and the resin pelletizer device further includes a report unit that reports the occurrence of the cavitation when the determination unit determines that the output value of the sensor less than the first threshold, and is equal to or more than the second threshold, and a stop control unit that stops the operation of the resin pelletizer device when the determination unit determines that the output value of the sensor is less than the second threshold.

The output value of the sensor decreases as the rotation number of the rotary blade increases while the cavitation occurs. This may be attributed to an increase in the fluttering of the rotary blade. As the fluttering of the rotary blade increase, a degree of defective cutting further increases. For example, a plurality of pellets connected in a chain form is produced. This causes a stick of the pellets inside the resin pelletizer device.

Thus, when the determination unit determines that the output value of the sensor is less than the first threshold, and equal to or more than the second threshold, it is considered that a serious problem does not occur to the resin pelletizer device (a pellet having tails is produced for defective cutting), and the report unit reports the occurrence of the cavitation. In contrast, when the determination unit determines that the output value of the sensor is less than the second threshold, it is considered that a serious problem occurs to the resin pelletizer device (a plurality of pellets connected in the chain form is produced for defective cutting, for example), and the stop control unit automatically stops the operation of the resin pelletizer device.

In the above-mentioned configuration, the resin pelletizer device further includes a storage unit that stores beforehand an upper limit value of the rotation number of the rotary blade at which the cavitation does not occur, and a rotation control unit that controls the rotation number of the rotary blade to a value which is not more than the upper limit value.

With this configuration, the cavitation can be prevented from occurring.

A cavitation monitoring method according to a second aspect of the present invention is a method of monitoring cavitation occurred in a resin pelletizer device includes a die including a die surface in which a die hole is formed, and a rotary blade that rotates on a die surface in the water, thereby cutting resin extruded from the die hole in the water into a pellet form, and including a first step of detecting an elastic wave generated during the rotation of the rotary blade on the die surface, and a second step of monitoring an amplitude of the elastic wave detected in the first step, and determining that cavitation occurs when the amplitude of the elastic wave becomes less than a predetermined threshold.

The cavitation monitoring method according to the second aspect of the present invention prescribes the resin pelletizer device according to the first aspect of the present invention from a point of view of method, and provides the same advantageous effects as those of the resin pelletizer device according to the first aspect of the present invention.

According to the present invention, the cavitation occurring to the resin pelletizer device can be monitored.

BRIEF DESCRIPTION OF THE DRAWINGS

FIG. 1 is a block diagram of a configuration of a resin pelletizer device according to an embodiment.

FIG. 8 is a flowchart of control of the resin pelletizer device by using a first threshold and a second threshold.

DESCRIPTION OF THE PREFERRED EMBODIMENTS

Figure 2:
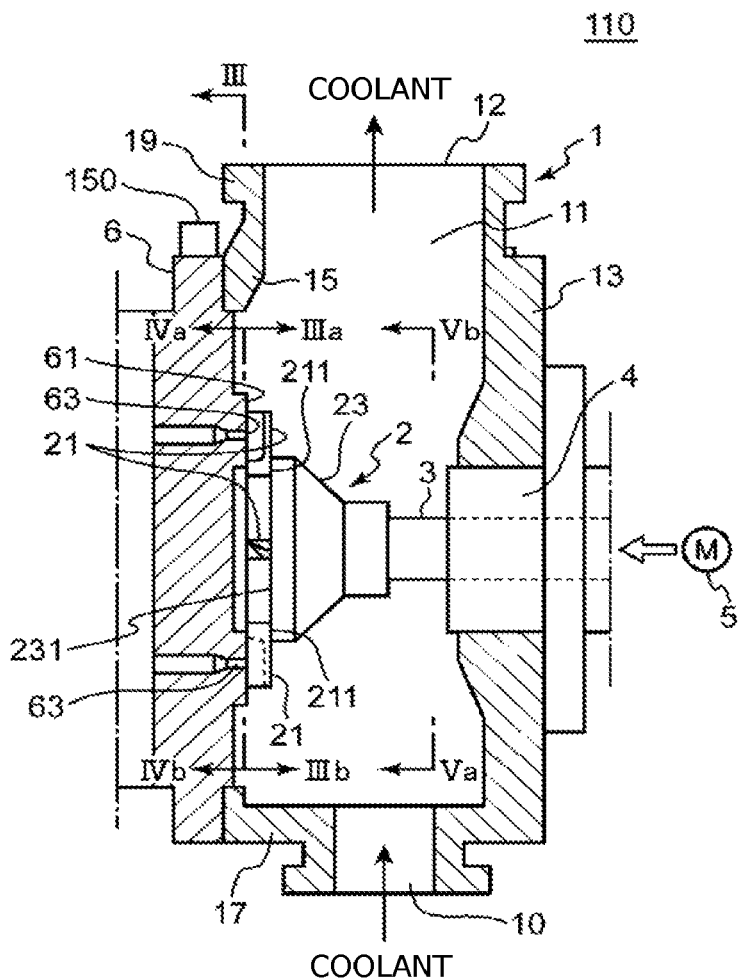
FIG. 2 is a cross sectional view of a resin pelletizer device main unit.

Hereinafter, an embodiment of the present invention will be described in details with reference to the drawings. FIG. 1 is a block diagram of a configuration of a resin pelletizer device 100 according to the embodiment. The resin pelletizer device 100 includes a resin pelletizer device main unit 110, a control unit 120, an operation panel 130, a report unit 140, and a sensor 150.

Figure 3:
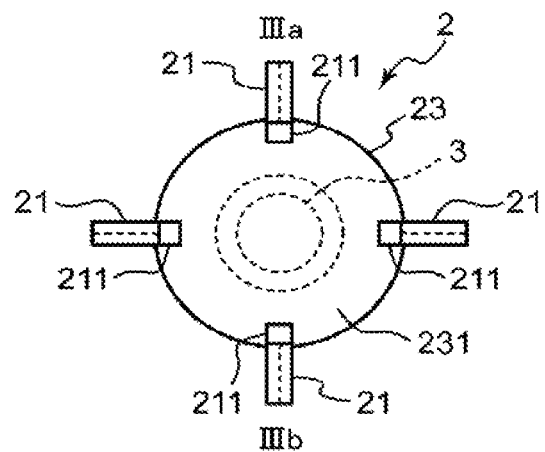
FIG. 3 is a plan view made in a direction indicated by arrows IIIa and IIIb in FIG. 2.
Figure 4:
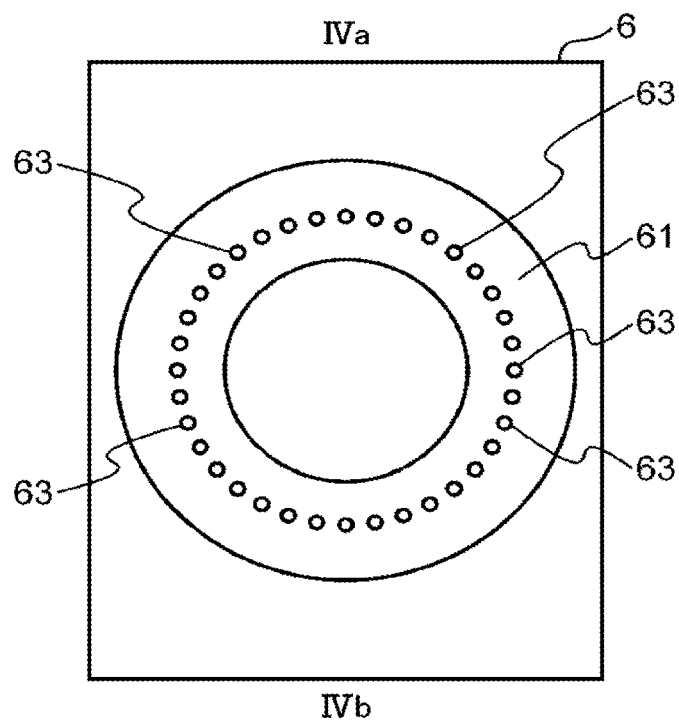
FIG. 4 is a plan view made in a direction indicated by arrows IVa and IVb in FIG. 2.
Figure 5:
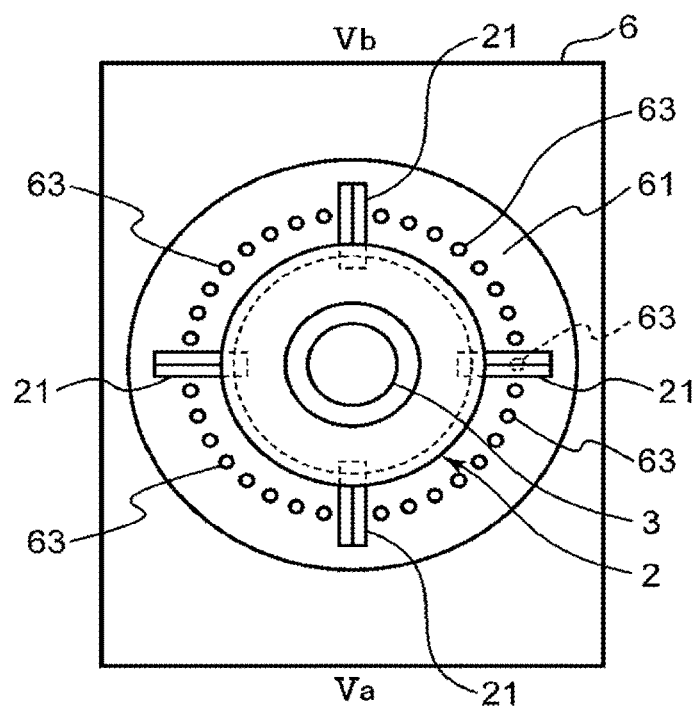
FIG. 5 is a plan view made in a direction indicated by arrows Va and Vb in FIG. 2.

A description will first be given of the resin pelletizer device main unit 110. FIG. 2 is a cross sectional view of the resin pelletizer device main unit 110. FIG. 3 is a plan view made in a direction indicated by arrows IIIa and IIIb in FIG. 2. FIG. 4 is a plan view made in a direction indicated by arrows IVa and IVb in FIG. 2. FIG. 5 is a plan view made in a direction indicated by arrows Va and Vb in FIG. 2.

Referring to FIG. 2, the resin pelletizer device main unit 110 includes a chamber 1, a rotary head 2, a rotation shaft 3, a bearing 4, a motor 5, and a die 6. The rotary head 2 is arranged in an interior 11 of the chamber 1. The rotary head 2 is fixed to one end of the rotation shaft 3. A through hole is formed on a wall surface 13 of the chamber 1 crossing the rotation shaft 3, and the bearing 4 is fitted thereto. The bearing 4 supports the rotation shaft 3. The other end of the rotation shaft 3 extends to the outside of the chamber 1, and is coupled to the motor 5. When the motor 5 rotates, the rotation shaft 3 rotates, thereby rotating the rotary head 2.

Referring to FIGS. 2 and 3, the rotary head 2 includes four rotary blades 21 and a fixing portion 23 to which the respective rotary blades 21 are fixed. The fixing portion 23 has a frustoconical shape, and the rotation shaft 3 is fixed to one end surface of the fixing portion 23. The four rotary blades 21 are arranged at an interval of 90 degrees on the other end surface (bottom surface 231 of the conical frustum) of the fixing portion 23. Though a description is given of a case where the number of the rotary blades 21 is four as an example, the number of the rotary blades 21 is not limited to four.

Each rotary blade 21 has an approximately rectangular shape, and a longitudinal direction of the rotary blade 21 is oriented in a radial direction of the other end surface (bottom surface 231 of the conical frustum) of the fixing portion 23. One end 211 of the rotary blade 21 is fixed to an edge portion of the other end surface (bottom surface 231 of the conical frustum) of the fixing portion 23, and the rotary blade 21 rotates outside of the other end surface (bottom surface 231 of the conical frustum) of the fixing portion 23.

A through hole is formed on a wall surface 15 of the chamber 1 opposing the other end surface (bottom surface 231 of the conical frustum) of the fixing portion 23. This through hole is blocked by the die 6.

Referring to FIGS. 2 and 4, the die 6 has a die surface 61 arranged in the interior 11 of the chamber 1. The die surface 61 has a disk shape, and a plurality of die holes 63 is formed at an equal interval on a circle on the die surface 61. The die holes 63 pass through the die 6. Referring to FIGS. 2 and 5, the die holes 63 are formed on a path along which the rotary blades 21 rotate, and molten resin extruded by an extruder (not shown) passes through the die holes 63, is extruded from the die holes 63, and is cut by the rotary blades 21 on the die surface 61. As a result, the molten resin is formed into pellets.

Referring to FIG. 2, the interior 11 of the chamber 1 is filled with the water during the operation of the resin pelletizer device 100, and the rotary head 2, the die surface 61, and the die holes 63 are in the water. The pellets are cooled by the water in the interior 11 of the chamber 1. A through hole serving as an inflow port 10 is formed on a wall surface 17 of the chamber 1 in a bottom portion of the chamber 1. A through hole serving as an outflow port 12 is formed on a wall surface 19 of the chamber 1 in a top portion of the chamber 1. The water is fed from the inflow port 10 to the interior 11 of the chamber 1, the interior 11 is thus filled with the water, and the water in the interior 11 is led from the outflow port 12 to the outside of the chamber 1, and is again fed from the inflow port 10 to the interior 11 of the chamber 1.

Referring to FIG. 1, a description is now given of the control unit 120. The control unit 120 controls the resin pelletizer device main unit 110. The control unit 120 is a computer realized by a CPU (Central Processing Unit), a RAM (Random Access Memory), a ROM (Read Only Memory), and the like. The control unit 120 includes, as functional blocks, a determination unit 121, a rotation control unit 123, a storage unit 125, and a stop control unit 127. A description will be given of these functional blocks later.

The operation panel 130 is a device on which an input of operating the resin pelletizer device 100 is carried out. The input includes a command of starting the operation of the resin pelletizer device 100, a command of stopping the operation, and setting the rotation number of the rotary blades 21.

When cavitation is determined to have occurred during the operation of the resin pelletizer device 100, the report unit 140 reports the occurrence of the cavitation. The report unit 140 is realized by a display, a speaker, an alarm lamp, or the like. When the report unit 140 is the display, an image indicating the occurrence of the cavitation is displayed. When the report unit 140 is the speaker, a sound indicating the occurrence of the cavitation is output. When the report unit 140 is the alarm lamp, the alarm lamp turns on.

Referring to FIGS. 1 and 2, the sensor 150 is arranged on a side surface of the die 6. The resin pelletizer device 100 uses the sensor 150 to monitor the cavitation. A detailed description is now given. An ultrasonic wave is generated during the rotation of the rotary blades 21 on the die surface 61. Though a predetermined clearance is provided between the rotary blade 21 and the die surface 61, a main cause of the contact between the rotary blades 21 and the die surface 61 is considered to be a vibration in an axial direction of the rotation shaft 3 for rotating the rotary blades 21 during the rotation of the rotary blades 21 on the die surface 61.

The sensor 150 detects an elastic wave generated during the rotation of the rotary blades 21 on the die surface 61 (an elastic wave generated by the contact between the rotary blades 21 and the die surface 61 during the rotation of the rotary blades 21 on the die surface 61). If the ultrasonic wave generated during the rotation of the rotary blades 21 on the die surface 61 is detected as the elastic wave, an AE (Acoustic Emission) sensor is used. If the vibration generated during the rotation of the rotary blades 21 on the die surface 61 is detected as the elastic wave, a vibration sensor is used. A description is given of an example in which the AE sensor is used as the sensor 150 according to this embodiment. The output value of the sensor 150 is an intensity of a signal output from the sensor 150, and represents the amplitude of the ultrasonic wave generated during the rotation of the rotary blades 21 on the die surface 61.

Figure 6:
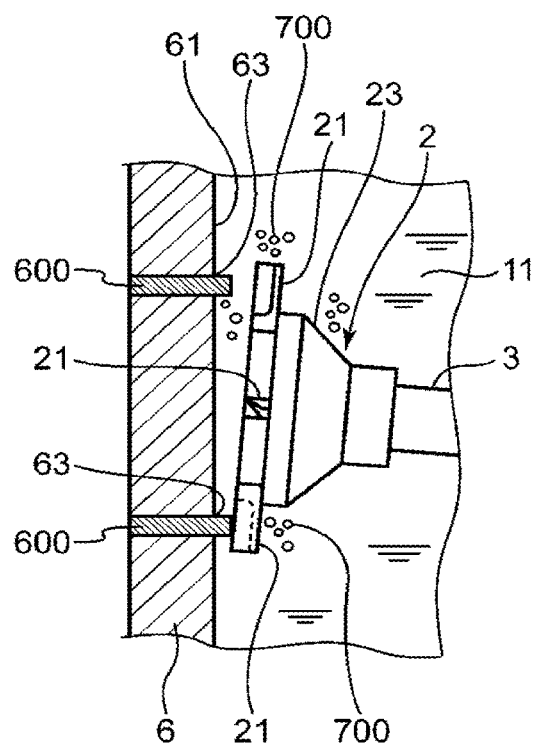
FIG. 6 is an explanatory diagram of cavitation occurred during an operation of the resin pelletizer device.

FIG. 6 is an explanatory diagram of the cavitation occurred during the operation of the resin pelletizer device 100. The rotary head 2 is rotating at a high speed in the state where the interior 11 of the chamber 1 is filled with the water during the operation of the resin pelletizer device 100, and the rotary blades 21 are thus rotating at the high speed on the die surface 61. Molten resin 600 extruded from the die holes 63 is cut by the rotary blades 21 to form pellets.

When the rotation number of the rotary blades 21 increases, the cavitation occurs. Reference numeral 700 denotes bubbles caused by the cavitation. As described above, the ultrasonic wave is generated during the rotation of the rotary blades 21 on the die surface 61. The ultrasonic wave generated on this occasion is detected by the sensor 150 (FIG. 1). The present inventor has found such a phenomenon that the output value (the intensity of the signal output from the sensor 150) of the sensor 150 increases as the rotation number of the rotary blades 21 increases, but the output value of the sensor 150 decreases when the cavitation occurs. This is considered to be caused by such a state that the cavitation occurs, and the rotary blades 21 thus flutter, resulting in a decrease in a contact pressure between the rotary blades 21 and the die surface 61.

A reason for the fluttering of the rotary blades 21 resulting from the occurrence of the cavitation is not clear. The present inventor estimates that a shock wave, which have been generated upon disappearance of the bubbles 700 formed by the cavitation, causes an inclination of the rotation shaft 3 for rotating the rotary blades 21, thereby fluttering the rotary blades 21.

Figure 7:
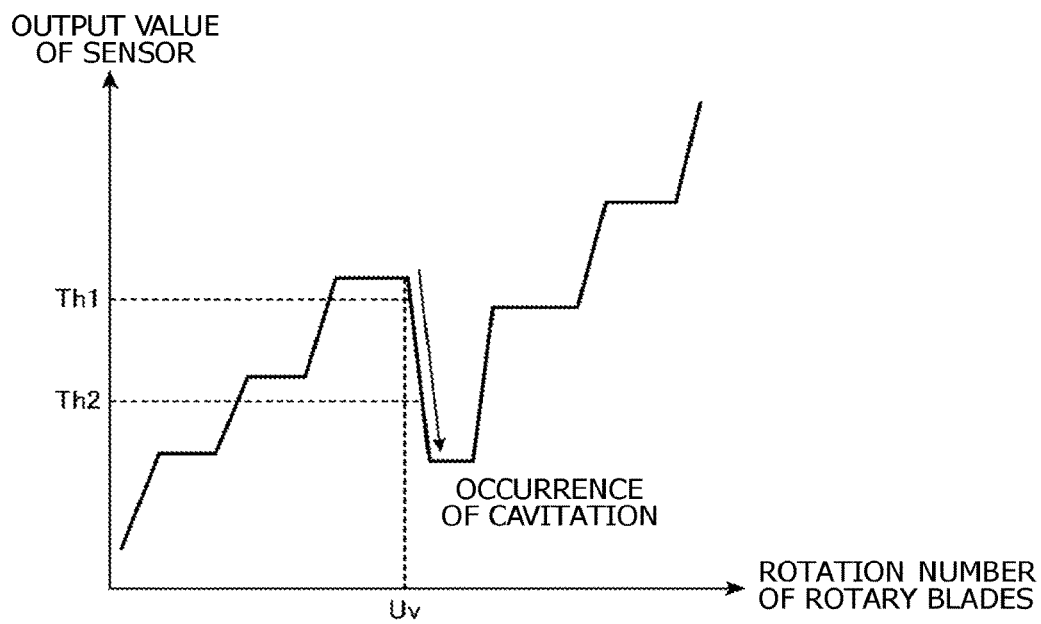
FIG. 7 is a chart of a relationship between the rotation number of rotary blades and an output value of a sensor.

FIG. 7 is a chart of a relationship between the rotation number of the rotary blades 21 (rotation number of the rotary head 2) and the output value of the sensor 150. The horizontal axis represents the rotation number of the rotary blades 21, and the vertical axis represents the output value of the sensor 150. As the rotation number of the rotary blades 21 increases, though the output value of the sensor 150 repeatedly increases and then stays constant, the output value of the sensor 150 sharply decreases upon the occurrence of the cavitation. The occurrence of the cavitation is appreciated from the generation of the bubbles 700 in a large amount.

The cavitation causes defective cutting. Thus, referring to FIG. 1, the determination unit 121 monitors the output value of the sensor 150, and determines that the cavitation occurs when the output value of the sensor 150 becomes more than a predetermined threshold (such as a first threshold Th1), and the output value of the sensor 150 then becomes less than the threshold. Thus, with the resin pelletizer device 100 according to the embodiment, the cavitation can be monitored.

According to this embodiment, the first threshold Th1 and a second threshold Th2 less than the threshold Th1 are set as thresholds for monitoring the cavitation. A description is given of this. Referring to FIG. 7, the output value of the sensor 150 decreases as the rotation number of the rotary blades 21 increases while the cavitation is occurring. This may be attributed to such a state that the fluttering of the rotary blades 21 increases, resulting the decrease in the contact pressure between the rotary blades 21 and the die surface 61. As the fluttering of the rotary blades 21 increases, a degree of defective cutting further increases. For example, a plurality of pellets connected in a chain form is produced. This causes a stick of the pellets in the interior 11 of the chamber 1 of the resin pelletizer device 100.

When the cavitation occurs, but a serious problem does not occur to the resin pelletizer device 100 (when a pellet having tails, for example, is produced for defective cutting), the first threshold Th1 and the second threshold Th2 are determined so that the output value of the sensor 150 is less than the first threshold Th1, and equal to or more than the second threshold Th2. In contrast, when the cavitation occurs, and a serious problem occurs to the resin pelletizer device 100 (a plurality of pellets connected in a chain form, for example, is produced for defective cutting), the second threshold Th2 is determined so that the output value of the sensor 150 is less than the second threshold Th2.

The first threshold Th1 and the second threshold Th2 are set in advance before the operation of the resin pelletizer device 100 starts. A detailed description is now given. Referring to FIGS. 1, 2, and 7, an operator operates the operation panel 130 to input a command of setting a threshold while the interior 11 of the chamber 1 is filled with the water. As a result, the rotation control unit 123 controls the rotation of the motor 5, thereby rotating the rotary blades 21. The molten resin is not fed to the die holes 63, and the molten resin is thus not extruded from the die holes 63.

The rotation control unit 123 provides control of gradually increasing the rotation number of the rotary blades 21. The determination unit 121 monitors the output value of the sensor 150, and stores the output value of the sensor 150 as the first threshold Th1 in the storage unit 125 when the output value of the sensor 150 decreases, and a decrease amount becomes more than a predetermined first amount. As a result, the setting of the first threshold Th1 is completed.

The determination unit 121 continues the monitoring of the output value of the sensor 150, and stores the output value of the sensor 150 as the second threshold Th2 in the storage unit 125 when the output value of the sensor 150 further decreases from the first threshold Th1, and the decrease amount becomes more than a predetermined second value. As a result, the setting of the second threshold Th2 is completed.

According to this embodiment, when the decrease amount of the output value of the sensor 150 becomes more than the first amount, the output value of the sensor 150 on this occasion is set to the first threshold Th1. However, the cavitation may occur even when the decrease amount of the output value of the sensor 150 is actually less than the first amount due to an error in the output value of the sensor 150 or the like during the operation of the resin pelletizer device 100. Thus, when the decrease mount of the output value of the sensor 150 becomes more than the first amount, a constant multiplication of the output value of the sensor 150 on this occasion may be set to the first threshold Th1. The same also applies to the second threshold Th2.

A description is now given of the control of the resin pelletizer device 100 using the first threshold Th1 and the second threshold Th2. FIG. 8 is a flowchart for illustrating the control. Referring to FIGS. 1 and 8, the determination unit 121 monitors the output value of the sensor 150 during the operation of the resin pelletizer device 100 (Step S1).

The determination unit 121 determines whether the output value of the sensor 150 monitored in Step S1 is more than the first threshold Th1 shown in FIG. 7 or not (Step S2). When the determination unit 121 determines that the output value of the sensor 150 monitored in Step S1 is not more than the first threshold Th1 (No in Step S2), the determination unit 121 carries out the processing in Step S1. On this occasion, the report unit 140 reports that the output value of the sensor 150 is not more than the first threshold Th1. The operator operates the operation panel 130 to adjust the rotation number of the rotary blades 21.

When the determination unit 121 determines that the output value of the sensor 150 monitored in Step S1 is more than the first threshold Th1 (Yes in Step S2), the determination unit 121 continues the monitoring of the output value of the sensor 150 (Step S3).

The determination unit 121 determines whether the output value of the sensor 150 monitored in Step S3 is less than the first threshold Th1 or not (Step S4). When the determination unit 121 determines that the output value of the sensor 150 monitored in Step S3 is equal to or more than the first threshold Th1 (No in Step S4), the determination unit 121 carries out the processing in Step S3.

When the determination unit 121 determines that the output value of the sensor 150 monitored in Step S3 is less than the first threshold Th1 (Yes in Step S4), the determination unit 121 determines whether the output value of the sensor 150 monitored in Step S3 is less than the second threshold Th2 or not (Step S5).

When the determination unit 121 determines that the output value of the sensor 150 monitored in Step S3 is equal to or more than the second threshold Th2 (No in Step S5), the report unit 140 reports the occurrence of the cavitation while the operation of the resin pelletizer device 100 continues (Step S6). Then, the determination unit 121 carries out the processing in Step S3.

When the determination unit 121 determines that the output value of the sensor 150 monitored in Step S3 is less than the second threshold Th2 (Yes in Step S5), the stop control unit 127 stops the operation of the resin pelletizer device 100 (Step S7). As a result, the rotation of the rotary blades 21 is stopped.

As described above, when the determination unit 121 determines that the output value of the sensor 150 is less than the first threshold Th1 (Yes in Step S2), and is equal to or more than the second threshold Th2 (No in Step S5), it is considered that a serious problem is not occurring to the resin pelletizer device 100 (a pellet having tails, for example, is produced for defective cutting), the operation of the resin pelletizer device 100 continues, and the report unit 140 reports the occurrence of the cavitation (Step S6).

In contrast, when the determination unit 121 determines that the output value of the sensor 150 is less than the second threshold Th2 (Yes in Step S5), it is considered that a serious problem occurs to the resin pelletizer device 100 (a plurality of pellets connected in the chain form is produced for defective cutting, for example), and the stop control unit 127 automatically stops the operation of the resin pelletizer device 100 (Step S7).

A description is now given of an upper limit value of the rotation number of the rotary blades 21. The occurrence of the cavitation mainly depends on the rotation number of the rotary blades 21. As the rotation number of the rotary blades 21 increases, the cavitation becomes severer.

Referring to FIG. 7, it is appreciated that the cavitation occurs when the rotation number of the rotary blades 21 becomes more than a predetermined value. Thus, the occurrence of the cavitation can be prevented by setting an upper limit value Uv of the rotation number of the rotary blades 21 to a value smaller than the predetermined value.

The upper limit value Uv is set before the operation of the resin pelletizer device 100 is started. A detailed description is now given. Referring to FIGS. 1, 2, and 7, the operator operates the operation panel 130 to input a command of setting the upper limit value Uv while the interior 11 of the chamber 1 is filled with the water. As a result, the rotation control unit 123 controls the rotation of the motor 5, thereby rotating the rotary blades 21. The molten resin is not fed to the die holes 63, and the molten resin is thus not extruded from the die holes 63.

The rotation control unit 123 provides control of gradually increasing the rotation number of the rotary blades 21. The determination unit 121 monitors the output value of the sensor 150, and when the output value of the sensor 150 decreases, and the decrease amount becomes more than a predetermined third amount, the rotation number of the rotary blades 21 on this occasion is considered as the rotation number at which the cavitation occurs, and a rotation number lower than this rotation number is stored as the upper limit value Uv in the storage unit 125. As a result, the setting of the upper limit value Uv is completed.

When the operator operates the resin pelletizer device 100, the operator can select any one of the control based on the first threshold Th1 and the second threshold Th2 or the control based on the upper limit Uv. When the operator operates the operation panel 130 to input a command of selecting the control by using the upper limit value Uv, the rotation control unit 123 provides such control that the rotation number of the rotary blades 21 does not become more than the upper limit value Uv stored in the storage unit 125 during the operation of the resin pelletizer device 100. As a result, the cavitation can be prevented from occurring.

Though the two thresholds (first threshold Th1 and the second threshold Th2) are set in this embodiment, the number of the thresholds may be one. A description is given of this configuration as a first variation and a second variation.

Referring to FIGS. 1 and 7, the determination unit 121 according to the first variation monitors the output value of the sensor 150, and determines that the cavitation occurs when the output value of the sensor 150 becomes less than a predetermined threshold (such as the first threshold Th1). The report unit 140 reports the occurrence of the cavitation when the determination unit 121 determines that the cavitation occurs. The first variation does not include the stop control unit 127.

The occurrence of the cavitation can be reported when the determination unit 121 determines that the cavitation occurs according to the first variation. Thus, the operator of the resin pelletizer device 100 can take a necessary action (such as an action of decreasing the rotation number of the rotary blades 21 and an action of stopping the operation of the resin pelletizer device 100) for responding to the cavitation occurrence.

Referring to FIGS. 1 and 7, the determination unit 121 according to the second variation monitors the output value of the sensor 150, and determines that the cavitation occurs when the output value of the sensor 150 becomes less than a predetermined threshold (such as the first threshold Th1). The stop control unit 127 stops the operation of the resin pelletizer device 100 when the determination unit 121 determines that the cavitation occurs. The second variation does not include the report unit 140.

The operation of the resin pelletizer device 100 can automatically be stopped when the determination unit 121 determines that the cavitation occurs according to the second variation.

What is claimed is:

1. A resin pelletizer device comprising:
    a die that includes a die surface in which a die hole is formed;
    a rotary blade that rotates on the die surface in the water, thereby cutting resin extruded from the die hole in the water into a pellet form;
    a sensor that detects an elastic wave generated during the rotation of the rotary blade on the die surface; and
    a determination unit that monitors an output value of the sensor, and determines that cavitation occurs when the output value of the sensor becomes less than a predetermined threshold.

2. The resin pelletizer device according to claim 1, further comprising a report unit that reports the occurrence of the cavitation when the determination unit determines that the cavitation occurs.

3. The resin pelletizer device according to claim 1, further comprising a stop control unit that stops an operation of the resin pelletizer device when the determination unit determines that the cavitation occurs.

4. The resin pelletizer device according to claim 1, wherein the determination unit sets a first threshold and a second threshold less than the first threshold as the thresholds, and compares the thresholds with the output value of the sensor, the resin pelletizer device further comprising:
    a report unit that reports the occurrence of the cavitation when the determination unit determines that the output value of the sensor is less than the first threshold, and equal to or more than the second threshold; and
    a stop control unit that stops the operation of the resin pelletizer device when the determination unit determines that the output value of the sensor is less than the second threshold.

5. The resin pelletizer device according to claim 1, further comprising:
    a storage unit that stores an upper limit value of the rotation number of the rotary blade at which the cavitation does not occur; and
    a rotation control unit that controls the rotation number of the rotary blade to a value which is not more than the upper limit value.

6. A method of monitoring cavitation to occur to a resin pelletizer device includes a die including a die surface in which a die hole is formed, and a rotary blade that rotates on a die surface in the water, thereby cutting resin extruded from the die hole in the water into a pellet form, the cavitation monitoring method comprising:
    detecting an elastic wave generated during the rotation of the rotary blade on the die surface; and
    monitoring an amplitude of the elastic wave detected in the first step, and determining that cavitation occurs when the amplitude of the elastic wave becomes less than a predetermined threshold.

* * * * *